United States Patent [19]

Halpern

[11] 4,424,172

[45] Jan. 3, 1984

[54] 5,5-BIS-(BROMOMETHYL)-2-HYDROXY-2-OXO-1,3,2-DIOXAPHOSPHORINANES AND PROCESS FOR PREPARING SAME

[75] Inventor: Yuval Halpern, Skokie, Ill.

[73] Assignee: Borg-Warner Chemicals, Inc., Parkersburg, W. Va.

[21] Appl. No.: 279,660

[22] Filed: Jul. 2, 1981

[51] Int. Cl.$^3$ .............................................. C07F 9/15
[52] U.S. Cl. .................................... 260/937; 260/983
[58] Field of Search ............................... 260/937, 983

[56] References Cited

U.S. PATENT DOCUMENTS

| | | | |
|---|---|---|---|
| 2,661,365 | 12/1953 | Gamrath et al. | 260/937 |
| 3,159,664 | 12/1964 | Bartlett | 260/937 |
| 4,007,236 | 2/1977 | Duffy et al. | 260/937 |
| 4,160,795 | 7/1979 | Albright et al. | 260/937 |

OTHER PUBLICATIONS

Meston, "J. Chem. Soci.", (1963), Dec. pp. 6059–6060.
Edmundson, "Tetrahedron," vol. 21, No. 9, (1965), pp. 2379–2387 (2384).

Primary Examiner—Anton H. Sutto
Attorney, Agent, or Firm—Joseph Shekleton

[57] ABSTRACT

A process for preparing 5,5-bis(halomethyl)-2-hydroxy-2-oxo-1,3,2-dioxaphosphorinanes by hydrolysis of the corresponding phosphoryl chloride. The product is effective, in small proportions, to impart flame-retardant properties to polymer compositions, especially polypropylene and styrenic polymers.

9 Claims, No Drawings

5,5-BIS-(BROMOMETHYL)-2-HYDROXY-2-OXO-1,3,2-DIOXAPHOSPHORINANES AND PROCESS FOR PREPARING SAME

This invention relates as indicated to a process for preparing certain dioxaphosphorinanes. It also relates to one of the dioxaphosphorinanes available from that process.

BACKGROUND OF THE INVENTION

The acid products of the process herein are useful as flame retardant additives in polymer compositions. Moreover, the salts of these acid products also are useful as flame retardants in polymer compositions.

Polymers vary widely in their resistance to burning. Some, such as the polyolefins, polystyrene, polyalkyl acrylates and methacrylates, and the like, burn readily. Polytetrafluoroethylene, polyvinylidene chloride and polyvinyl chloride, on the other hand, have a rather high resistance to burning. In any event, it obviously is highly desirable that, for certain applications, a polymer should have a high degree of flame retardance so that it will meet the requirements of various building codes or that it will meet safety standards imposed on toys, carpeting, drapery materials, automotive applications, etc.

The treatment of these more flammable polymers to increase their resistance to burning is well known; such treatment generally has involved the incorporation in the polymer composition of substantial proportions of antimony oxide, halogenated hydrocarbons and low molecular weight phosphate esters. Ordinarily, though, the effective use of these and other additives has required their presence in such high concentrations as to adversely affect the desirable properties of the polymer. Thus, such desirable properties as hardness, clarity, strength, elasticity, etc., are diminished significantly by the presence of large amounts of a flame retardant chemical.

The formulator's goal, in preparing a flame retardant polymer composition, is to add just enough of the flame retardant compound so as to provide the desired degree of flame retardance, but no more than this minimum amount, so as to preserve as much as possible the advantageous properties of the polymer. Frequently, it is not possible to select a flame retardant which will meet these requirements satisfactorily.

The preparation of 2,2-di(chloromethyl)trimethylene hydrogen phosphate by reaction of 2,2-di(chloromethyl)trimethylene glycol with polyphosphoric acid at 100° C. is shown in "Simple Syntheses of Cyclic Phosphate Esters" by A. M. Meston, J. Chem. Soc., 1963 (Dec.), 6059. The reaction required 16 hours.

U.S. Pat. No. 2,661,365 (Gamrath et al.) shows in very general terms the hydrolysis (with water) of alkanediol phosphoryl monochlorides to yield the corresponding alkanediol phosphoric acids. The alkanediol nucleus is a substituted trimethylene glycol residue wherein the substituents are alkyl groups.

The hydrolysis of 2-chloro-5,5-dimethyl-2-oxo-1,3,2-dioxaphosphorinane with aqueous acetone is shown in "Cyclic Organophosphorus Compounds-III" by R. S. Edmundson, Tetrahedron, 21 (9), 2379–87 (1965), at page 2384. The hydrolysis mixture is heated over steam for 1.5 hours and the product is the corresponding phosphoric acid.

SUMMARY OF THE INVENTION

The invention of the present application is a process for preparing a dihalo-substituted neopentyl phosphoric acid comprising reacting stoichiometric quantities of 5,5-bis-(halomethyl)-2-chloro-2-oxo-1,3,2-dioxaphosphorinane where the halo groups are bromine or chlorine, and water, and isolating from the resulting product mixture the desired phosphoric acid.

DETAILED DESCRIPTION OF THE INVENTION

The process ordinarily is carried out in a solvent and a wide variety of solvents is available. Acetonitrile and chlorobenzene are preferred solvents, but any relatively low-boiling (below 140° C.) solvent which is chemically inert to the reactants and product is suitable. Acetone, toluene, methylethylketone, ethyl acetate, dioxane, carbon tetrachloride, etc. are illustrative examples of useful solvents.

Where a water-immiscible solvent is used the reaction may be promoted by the presence of a phase transfer catalyst. Illustrative phase transfer catalysts include phosphonium and quaternary ammonium salts and bases such as tetrabutyl phosphonium bromide, tetramethyl phosphonium iodide, tetra-n-butyl phosphonium chloride, tetra-n-amyl phosphonium bromide, tetraisobutyl phosphonium hydroxide, tetraisobutyl phosphonium bromide, tetramethyl phosphonium nitrate, tetraethyl phosphonium sulfate, tetraethyl ammonium chloride, tetra-n-butyl ammonium bromide, tetraisopropyl ammonium hydroxide, tetramethyl ammonium nitrate and tetra-n-hexyl ammonium hydroxide. They act to promote better contact between the reactants.

At least enough water must be used in the process to provide a stoichiometric quantity with respect to the chloro reactant. Larger amounts, within reason, may be used.

In some instances, the presence of a small proportion, i.e., 0.1–1.0% of the phosphorinane reactant, of a low molecular weight, tertiary aliphatic amine assists the reaction. Trimethyl amine, triethylamine and triisopropyl amine are illustrative examples. Amines having fewer than 10 carbon atoms are contemplated. Yields are increased, reaction time is shortened and the reaction may be carried out at a lower temperature.

The temperature of the process desirably is above about 20° C. While it is possible to carry out the process at lower temperatures, the hydrolysis reaction proceeds so slowly as to be impractical. In general, the process is carried out at a temperature within the range of from about 20° C. to about 100° C.

The process is illustrated by the following examples.

EXAMPLE 1

A 100-ml., round-bottom, 3-necked flask fitted with a condenser, magnet bar stirrer and nitrogen inlet and outlet is charged with 6.85 g. (0.02 mol) of 5,5-bis(-bromomethyl)-2-chloro-2-oxo-1,3,2-dioxaphosphorinane and 55 ml. of acetonitrile and the resulting solution is stirred and heated to reflux temperature under a slow stream of dry nitrogen. Water, 0.36 ml. (0.02 mol), is injected into the refluxing solution and the evolved hydrogen chloride is monitored by trapping it in aqueous sodium hydroxide. One half the theoretical amount of hydrogen chloride is trapped within three hours. The reaction mixture is heated with continued stirring for an additional 48 hours, then cooled and filtered and the solid washed with 25 ml. of acetonitrile, then dried in vacuo at 50° C. (Yield: 2.48 g.). The filtrate is evaporated under reduced pressure to a white residue weighing 3.76 g. These solids are combined and crystallized from hot toluene to yield a product melting at 165°–170° C. It is identified as 5,5-bis(bromomethyl)-2-hydroxy-2-oxo-1,3,2-dioxaphosphorinane by means of $^{13}C$ nmr, elemental and mass spectrographic analysis.

EXAMPLE 2

A 500-ml., round-bottom, 3-necked flask fitted with a condenser, magnet bar stirrer, thermometer and nitrogen inlet and outlet, is charged with 65.5 g. (0.25 mol) of 2,2-(dibromomethyl)-1,3-propane-diol, 250 ml. of chlorobenzene and 23 ml. (0.25 mol) of phosphorus oxychloride. The mixture is stirred and heated at 95° C. for two hours during which time 60% of the theoretical amount of hydrogen chloride is evolved (and trapped in aqueous sodium hydroxide). Heating and stirring are continued for an additional 16 hours at the end of which time no more hydrogen chloride is evolved.

To this resulting clear solution there is added 4.5 ml. (0.25 mol) of water and heating (at 90° C.) and stirring continued for five hours during which time all of the theoretical amount of hydrogen chloride is evolved. The product mixture is cooled and filtered yielding a white precipitate which is washed with chlorobenzene and dried to a constant weight. The yield of 5,5-bis(bromomethyl)-2-hydroxy-2-oxo-1,3,2-dioxaphosphorinane melting at 165°–168° C. is 85% of the theory.

EXAMPLE 3

To a solution of 17 g. (0.05 mol) of 5,5-bis(bromomethyl)-2-chloro-2-oxo-1,3,2-dioxaphosphorinane in 25 ml. of toluene there is added 0.5 g. (0.0013 mol) of tetrabutyl phosphonium bromide in 30 ml. of water. The resulting mixture is stirred for 16 hours at room temperature, then filtered. A precipitate is collected, washed with heptane and dried in vacuo. The white solid is identified by means of infrared analysis as the desired 5,5-bis(bromomethyl)-2-hydroxy-2-oxo-1,3,2-dioxaphosphorinane. The yield of product melting at 156°–162° C. (165°–170° C. after crystallization from toluene) is 87% of the theory.

As noted earlier, the products available from the process of the invention are useful as flame retardant additives in polymer compositions. The bis(bromomethyl) acid is especially effective. The polymers especially susceptible to improvement, with respect to flame retardant properties imparted by the presence of small proportions of these additives, include principally polypropylene and styrene polymers. They are effective when used alone, or in combination with antimony trioxide.

The flame retardant products of the process herein should ordinarily be used in concentrations ranging from about 20 pph (parts per hundred parts of resin) to about 32 pph. When desired, antimony trioxide may be used as a synergist in concentrations ranging from about 2 pph to about 12 pph.

All parts and percentages herein, unless otherwise clearly expressed, are by weight.

I claim:

1. A dibromo-substituted neopentyl phosphoric acid having the structural formula:

$$\begin{array}{c} BrCH_2 \\ \diagdown \\ BrCH_2 \end{array} C \begin{array}{c} CH_2O \\ \diagdown \\ CH_2O \end{array} P \begin{array}{c} O \\ \diagup\!\!\!\diagup \\ \diagdown \\ OH \end{array}$$

2. A process for preparing a dihalo-substituted neopentyl phosphoric acid comprising reacting stoichiometric quantities of 2,2-bis-(halomethyl)-1,3-propane-diol and phosphorus oxychloride to form the 5,5-bis(halomethyl)-2-chloro-2-oxo-1,3,2-dioxaphosphorinane, reacting said dioxaphosphorinane, in a solvent, with water to form the 5,5-bis(halomethyl)-2-hydroxy-2-oxo-1,3,2-phosphorinane product, and isolating said product, the halo in each case being bromo or chloro.

3. A process for preparing a dihalo-substituted neopentyl phosphoric acid comprising reacting stoichiometric quantities of 5,5-bis-(halomethyl)-2-chloro-2-oxo-1,3,2-dioxaphosphorinane where the halo groups are bromine or chlorine, and water, in a solvent, and isolating from the resulting product mixture the desired phosphoric acid.

4. The process of claim 3 wherein the solvent is acetonitrile.

5. The process of claim 3 wherein the solvent is chlorobenzene.

6. The process of claim 3 characterized further in that it is carried out at a temperature above about 20° C.

7. The process of claim 3 wherein both halo groups are bromine.

8. The process of claim 3 wherein a phase transfer catalyst is used.

9. The process of claim 8 wherein the phase transfer catalyst is a phosphonium or quaternary ammonium salt or base.

* * * * *